United States Patent [19]

Johnson et al.

[11] Patent Number: 5,508,180

[45] Date of Patent: *Apr. 16, 1996

[54] BIOCATALYTIC OXIDATION USING SOYBEAN PEROXIDASE

[75] Inventors: Mark A. Johnson, Chillicothe; Alexander R. Pokora, Pickerington; William L. Cyrus, Jr., Ray, all of Ohio

[73] Assignee: Enzymol International, Inc.

[*] Notice: The term of this patent shall not extend beyond the expiration date of Pat. No. 5,147,793.

[21] Appl. No.: 308,082

[22] Filed: Sep. 16, 1994

Related U.S. Application Data

[62] Division of Ser. No. 49,580, Apr. 19, 1993, Pat. No. 5,391,488.

[51] Int. Cl.$^6$ .......................... C12P 13/00; C12P 11/00; C12P 7/24; C12N 9/08

[52] U.S. Cl. .................... 435/128; 435/130; 435/132; 435/147; 435/156; 435/192

[58] Field of Search .................................. 435/147, 192, 435/128, 130, 132, 156

[56] References Cited

U.S. PATENT DOCUMENTS

| | | | |
|---|---|---|---|
| 3,947,324 | 3/1976 | Lakshminarayanan | 195/66 R |
| 3,957,424 | 5/1976 | Zeffren et al. | 8/10.2 |
| 4,647,952 | 3/1987 | Pokora et al. | 346/210 |
| 4,900,671 | 2/1990 | Pokora et al. | 435/156 |
| 5,147,793 | 9/1992 | Johnson et al. | 435/156 |
| 5,188,953 | 2/1993 | Johnson et al. | 435/156 |

OTHER PUBLICATIONS

Mason et al, Bioch. Biophys. Acta 24:225–226 (1957).
Sessa et al, J. Agric. Food Chem. 29:960–965 (1981).
Gillikin et al, Plant Phys. 96(1):214–220 (1991).
Alberti, et al. "Enzymatic Removal of Dissolved Aromatics from Industrial Aqueous Effluents", Biotechnology and Bioengineering Symp., 11, 373–379 (1981).
Klivanov, et al. "Enzymatic Removal of Toxic Phenols and Anilines from Waste Water", J. Applied Biochem. 2, 414–421 (1980).
Alberti, et al., "Peroxidase for Removal of Hazardous Aromatics from Industrial Wastewaters", Biological Detoxication, 349–356.
Booth et al. "Studies in Peroxidase Action, Part X, The Oxidation of Phenols", JACS, 940–948 (1956).
Gillikan et al. "Purification of the Major Anionic Peroxidase Isozyme from Soybean Seed and Analysis of Its Developmental and Tissue–Specific Accumulation", Plant Physol. 89:53 (1989).
Singh et al., "Biocatalytic Oxidation of Hydroquinone to P Benzoquinone . . . System", pp. 663–664, vol. 7, No. 9 (1985).
Dordick et al. "Polymerization of Phenols Catalyzed by . . . Media", vol. XXX, pp. 31–36 (1987).
Patent Abstracts of Japan, vol. 14, No. 254 (C–724) May 31, 1990 and JP–A–20 72 874 (Koken Co. Ltd.) Mar. 13, 1990.
Database WPIL, Section Ch, Week 16, 1990, Derwent Publications, Ltd., London GB: Class D, AN 121042 & JP–A–2–72 874 (Koken) Mar. 13, 1990.
European Search Report EP 91 30 9652.

*Primary Examiner*—David M. Naff
*Assistant Examiner*—Francisco C. Prats
*Attorney, Agent, or Firm*—Thompson, Hine and Flory

[57] ABSTRACT

Biocatalytic oxidative processes wherein oxidizable substrates are reacted in the presence of soybean peroxidase are described. Preferred biocatalytic oxidative reactions include the oxidation of sulfides, O-dealkylation of alkyl aryl ethers, N-dealkylation of aromatic amines, halogenation of halogen-reactive compounds and polymerization of aromatic amines. Examples of such reactions include the oxidation of alkyl aryl sulfides, the O-dealkylation of methoxybenzenes, the N-dealkylation of N,N-dimethyl aromatic amines halogenation of 5,5-dimethyl 1,3-cyclohexane dione, and the polymerization of aniline which can yield an intrinsically conductive polymer (ICP). A solution of substrate is prepared and then contacted with soybean peroxidase in the presence of a peroxide, preferably hydrogen peroxide. The reactions are preferably carried out in the presence of 10 to 100 mM calcium ions.

16 Claims, No Drawings

BIOCATALYTIC OXIDATION USING SOYBEAN PEROXIDASE

This is a divisional of application Ser. No. 08/049,580, filed Apr. 19, 1993, now U.S. Pat. No. 5,391,488.

BACKGROUND OF THE INVENTION

The present invention relates to an improved biocatalytic process for the preparation of phenolic resins using soybean peroxidase and more generally to a biocatalytic process for oxidizing phenols and other compounds using soybean peroxidases.

The present invention further relates to a method for treating peroxidase enzymes so that they may be used in applications where the untreated enzyme could not previously be employed. More particularly, it relates to a method for treating a peroxidase enzyme source with a purifying agent to reduce the amount of impurities in the enzyme and thereby reduce contamination in processes using such enzymes as a biocatalyst.

U.S. Pat. No. 4,900,671 commonly assigned to the Mead Corporation discloses a method for preparing a phenolic resin which comprises preparing a solution of a phenol in a water miscible or immiscible solvent and an aqueous solution of a peroxidase or oxidase enzyme, mixing the two solutions and adding a peroxide or oxygen. The preferred method described in this patent makes use of horseradish peroxidase. The reaction is preferably carried out in a mixed solvent system. The peroxidase is dissolved in water, the phenol is dissolved in a solvent which may be water miscible or water immiscible. Hydrogen peroxide is added to the system and reaction occurs on the enzyme. It has now been found that soybean peroxidase is much more economical to use in this method. It has also been found that the quality of resin obtained from this method can be improved if the peroxidase is treated as described herein.

Alberti and Klibanov, BIOLOGICAL DETOXICATION, Chapter 22, Peroxidase for Removal of Hazardous Aromatics from Industrial Wastewaters, (1982), discloses that phenols can be removed from wastewaters as high molecular weight polymers by the action of peroxidase enzymes. The disclosed method relies on the ability of peroxidase enzyme to catalyze, with hydrogen peroxide, the oxidation of a variety of phenols and aromatic amines. Phenolic and aromatic amine free radicals are generated, which diffuse from the active center of the enzyme into solution, and polymerize to polyaromatic products. These high molecular weight polymers are water-insoluble and can be readily separated by filtration from water.

In the past, peroxidase enzymes have not been available at a cost and in a purity amenable to many biocatalytic processes. For example, horseradish roots, a common source of horseradish peroxidase, are cultivated generally in small quantities and are propagated through root cuttings, thus making it difficult to scale up production. The limited availability of the horseradish root extract coupled with the shortage of alternative sources of enzyme has created a very expensive market for such enzymes. Accordingly, there exists in the marketplace a need for an abundant and relatively inexpensive source of peroxidase.

SUMMARY OF THE INVENTION

A principal object of the present invention is to improve the biocatalytic oxidative process for preparing phenolic resins described in U.S. Pat. No. 4,900,671 through the use of peroxidases from soybeans and other legumes and plants. It has been found that soybean peroxidase has better temperature and solvent stability than horseradish peroxidase and that it is much more economical because it can be obtained from soybean hulls which are very inexpensive. This finding suggests that peroxidase from other sources and particularly legumes may also be advantageously used in the process.

A more general object of the present invention is to provide biocatalytic oxidative processes using soybean peroxidase or peroxidases from other legumes, rice, and plants (e.g., malvaceous plants such as cotton, see Egley, G. H., et al., *Planta* 157:224–232 (1983)). One such oxidative process is oxidative coupling of phenols and aromatic amines, however, there are other oxidative processes in which peroxidases have been used in which soybean peroxidase and other plant and legume peroxidases can be advantageous including wastewater treatment, oxidation of aromatic amines and others.

Still another object of the invention is to provide novel processes for biocatalytic oxidation wherein oxidation is carried out in the presence of the hulls of a legume which produces peroxidase, a particularly preferred legume hull is soybean hulls. It has been found that in many cases it is not necessary to remove peroxidase from the hull by extraction but that the hull can be directly introduced to the reaction medium where the peroxidase is available as an immobilized enzyme or by in situ extraction to catalyze the oxidative process.

Another object of the invention is to improve biocatalytic processes employing peroxidases by treating the peroxidase to remove non-peroxidase proteins and other lipophilic materials. These contaminants interfere with many biocatalytic processes by discoloring the reaction product. They can also lead to emulsification of the reaction system when the reaction is performed in aqueous media making it difficult to control the molecular weight and molecular weight distribution of the product and making it difficult to separate the product (See Example 2). In accordance with one aspect of the invention, peroxidase as a solution in water, is treated with protein fixatives or detergents to remove the unwanted materials. In another method, the peroxidase is treated with activated carbon.

Accordingly, one manifestation of the present invention is an improved process of biocatalytic oxidation wherein an oxidizable substrate is reacted with a peroxide in the presence of a peroxidase wherein the peroxidase is a peroxidase of a legume (plants of the family Leguminoseae) and, more particularly, soybean peroxidase, rice, or a plant of the family Malvaceae.

Another manifestation of the present invention is a process for preparing a phenolic resin which comprises reacting a phenol with soybean peroxidase or another of the aforementioned peroxidases in the presence of a peroxide. In a preferred embodiment of the invention, this reaction is carried out in a mixed solvent of water and a water miscible or a water immiscible solvent. In another embodiment of the invention, the peroxidase is supplied to the reaction as soybean or other legume hulls. Other embodiments of the invention utilize peroxidases from rice and malvaceous plants such as cotton.

Another manifestation of the invention is a process for treating peroxidase to remove proteinaceous or lipophilic contaminants and render it more useful in biocatalytic processes which comprises preparing a solution of a peroxidase and a protein fixative or a detergent, adding a non-solvent for the peroxidase, re-dissolving the peroxidase and separating the peroxidase from the contaminants.

In another embodiment of the invention, the peroxidase is purified by making a slurry of a peroxidase solution with activated carbon and removing the activated carbon.

Other objects and advantages will be apparent from the following description and the appended claims.

DEFINITION

The term "phenolic resin" as used herein includes phenolic dimers and trimers as well as higher molecular weight species.

A "unit" of peroxidase means the amount of peroxidase which produces a change of 12 absorbance units measured at 1 cm pathlength in one minute at 420 nm when added to a solution containing 100 mM potassium phosphate, 44 mM pyrogallol and 8 mM hydrogen peroxide and having a pH of 6 (Sigma Chemical Co. Peroxidase Bulletin).

DETAILED DESCRIPTION OF THE INVENTION

In the preferred embodiments of the invention, the peroxidase is soybean peroxidase, however, peroxidases from other legumes are also useful such as peroxidases from peas, guar beans, garbanzo beans, runner beans and the non-legume, rice. It is also believed that peroxidases from certain malvaceous plants such as cotton may be useful. The purification techniques described herein, in addition to being effective for peroxidases extracted from legumes, rice and malvaceous plants are also useful with horseradish peroxidase, haloperoxidases including chloroperoxidases, lactoperoxidases, bacterial peroxidases, and fungal ligninase.

Peroxidases, being water soluble, are easily harvested by homogenizing the protein source with water, filtering the homogenate, and retaining the filtrate.

The filtrate is treated to remove proteinaceous and lipophilic impurities by adding to the filtrate a solution of a protein fixative or a detergent and forcing the enzyme to precipitate by the addition of a non-solvent for the peroxidase such as acetone or isopropanol. The protein fixative and detergent both preferentially render the protein contaminants insoluble in water. The detergent also insolublizes non-protein lipophilic impurities. After addition of the fixative or detergent, a non-solvent for peroxidase is added to the solution to force the peroxidase and impurities to precipitate. The precipitate is separated, water is added to redissolve preferentially the peroxidase and the sample is centrifuged. The peroxidase is recovered as the supernatant solution. While these treatments probably do not completely remove impurities, they reduce them to a level that the oxidation product obtained using the peroxidase is improved in quality.

When using the detergent, the precipitate is preferably treated with a solution of phenol and a small amount of hydrogen peroxide. This appears to cause the phenol to interact with the detergent and enhance the binding of the impurities. After about one hour the sample is centrifuged to remove the impurities. The peroxidase is recovered in the supernatant solution. These processes may be repeated to further purify the enzyme.

The protein fixatives useful in treating the peroxidase include tannic acid, tannins, monolignols, fulvic acids, lignan, humic acids, melanoidins, proanthcyanidins, stilbenes, depsides, lignin model compounds, soluble suberin, flavonoids, soluble lignin, dihydroxyphenyl compounds, kerogen, gallic acid esters, phenolic acids, gallic acid amides, dihydric phenols, hexahydroxydiphenic glucose esters, polymeric phenols, bis (hydroxyphenyl) sulfones, bitumens, soluble lignite extracts, sulfonated phenols and naphthols and their copolymers, melamine/glyoxal/glyoxylate/phenol/naphthol condensates; vegetable extractives, especially rhubarb, mimosa, peat, euphorbia, cassia, rose, tea, grape and saxifragea; sulfonated extractives, especially of mimosa wood; and bark extractives, such as oak, eucalyptus, fig, cedar, spruce, pine, walnut, mulberry and chestnut; and graft copolymers derived from these extracts. Others include synthetic phenolic tanning agents (syntans) such as tanigan, tamol, ledertan, blancotan, basyntan, neosyn and nubuctan and phenolic compounds that cause melanization or sclerotization of proteins, especially catechol and dopamine amides, quinones, quinone methides, prenylated phenols and quinones and polymers derived from their oxidation, e.g., melanins and sclerotins, and the like.

Useful detergents include sodium dodecyl sulfate, sodium caprylate, sodium cholate, sodium decanesulfonic acid, sodium deoxycholate, sodium glycocholate, sodium deoxyglycocholate, sodium taurocholate, sodium taurodeoxycholate, cetylpyidinium chloride, dodecyltrimethyl ammonium, CHAPS, CHAPSO, dioctyl sulfosuccinate, alginic acid. Phenols useful to enhance detergent purification include t-butylphenol and bisphenols such as bisphenol A.

Removal of the impurities can be enhanced by adding a salt such as potassium chloride to the aqueous solution of the enzyme in an amount of about 1 to 10%. For certain protein fixatives such as the phenols which are not soluble in water, a small amount of a solvent such as an alcohol may be used to dissolve these fixatives in water as shown in Examples 5–9 below.

Non-solvents of the peroxidase are used to force the enzyme to precipitate and enable its separation. Useful non-solvents may be water miscible or water immiscible, however, they are preferably water miscible. Representative examples include acetone, isopropanol, n-propanol, methanol, and ethanol.

To purify the enzyme, peroxidase is added to water in an amount of about 400 units per ml water. When the protein fixative is used, it is generally added to the enzyme solution in an amount of about 1% to 10% based on weight of fixative to volume of enzyme (kg. to 1). Similar amounts of detergent are employed. The volume of the non-solvent which must be added to the enzyme solution to separate the enzyme will vary with the nature of the non-solvent but generally 1 to 10 volumes of non-solvent per volume of enzyme solution is required.

One oxidative process for preparing phenolic resin in accordance with the present invention comprises preparing separate solutions of the phenol, enzyme, and peroxide, and mixing them. The phenol is typically dissolved in an organic solvent, and the enzyme and peroxide are typically dissolved in water. The solutions may be gradually added to a common reaction vessel, but in a preferred method solutions of the phenol and the enzyme are pre-mixed and the peroxide solution is gradually added thereto. The enzyme may also be provided on a solid support or legume hulls may be used directly. The process may be carried out on a batch or continuous basis. In any process it is important to limit the rate of addition of the peroxide since excess peroxide tends to inhibit the reaction.

The amount of the enzyme used to make the phenolic resin will depend on its activity. The enzyme is not consumed in the reaction but gradually loses activity during the course of reaction. For practical purposes, the enzyme can be reacted in an amount of about 500 to 500,000 and more typically 1000 to 5000 units per 100 grams phenol. In other oxidative reactions, analogous amounts of the peroxidase will be used.

The peroxide used is typically hydrogen peroxide, but other peroxides are also useful. Examples of other potentially useful peroxides include methyl peroxide, ethyl peroxide, etc.

The peroxide is reacted in an amount of about 0.1 to 2.5 moles per mole phenol (or other oxidizable substrate) and, more typically, about 0.1 to 1.0 moles per mole phenol. Depending upon the nature of the oxidizing agent, it is reacted neat or as a solution. The preferred oxidizing agent, hydrogen peroxide, is dissolved in water. Its concentration may range form about 1 mM to 10M.

The substrate can be reacted in an aqueous medium or it can be reacted in an organic medium which may be a water-miscible or a water-immiscible solvent. Representative examples of useful water-immiscible solvents include hexane, trichloromethane, methyl ethyl ketone, ethyl acetate, and butanol. Examples of useful water-miscible solvents include ethanol, methanol, dioxane, tetrahydrofuran (THF), dimethyl formamide, methyl formate acetone, n-propanol, isopropanol, ethanol, t-butyl alcohol. The reaction is typically carried out at phenol concentrations of about 1 to 100 g per 100 ml solvent.

A number of different procedures may be used to react the phenol or other oxidizable substrate. Solutions of the phenol, enzyme, and peroxide may be individually prepared and metered into a reaction vessel, or solutions of the phenol and enzyme may be pre-mixed and the peroxide gradually added thereto. Alternatively, the enzyme and the phenol may be dissolved in a common solvent and the peroxide added later. Those skilled in the art will appreciate that a number of different reaction/mixing sequences are useful. The peroxide should be added at a controlled rate which is approximately equal to the rate at which it is consumed such that the concentration of the peroxide does not build to a level at which it undesirably inhibits the reaction and inactivates the enzyme.

The organic-aqueous system formed upon mixing the phenol, enzyme and peroxide may contain water and an organic solvent in a volumetric ratio (water:organic) in the range of about 1:10 to 10:1, more typically, 1:2 to 2:1. The most preferred ratio will vary with the nature of the phenolic monomer(s) that is (are) polymerized.

As indicated earlier, the legume hulls are biocatalytically active and can be used directly. It is not clear whether the peroxidase is being extracted by the reaction solvent medium or whether the peroxidase reacts similar to an immobilized enzyme. A combination of both mechanisms may occur.

Washing and extraction of the soybean hulls are preferably accomplished using hard water and, preferably, water containing calcium ions such as calcium chloride. It has been found that soybean peroxidase is more stable upon storage when it has been obtained from a solution in water containing calcium ions. It is believed that the calcium ions retain the heme group in the enzyme. The calcium ion can be present at a concentration of up to about 50 mM or more, preferably, about 0.1 to 20 mM and still more preferably about 5 to 15 mM.

The amount of hulls used will depend on their reactivity. To prepare the hulls for the reaction, they are preferably crushed and washed with toluene and added to ammonium sulfate solution as illustrated in Example 14 below. Aged hulls may work as well as fresh ones. The reaction may be carried out by simply preparing a slurry of the hulls in an aqueous solution of the phenol and gradually adding peroxide thereto at a controlled rate which does not result in reaction inhibition. Alternatively, the hulls can be packed in a column and peroxide and the oxidizable substrate passed over them to yield the oxidized product.

Variations in the way the hulls are prepared produce color developer resins with either low or high natural color. Hulls added to 840 ml 0.2 to 0.4M ammonium sulfate or sodium sulfate produced much lighter resin. Hulls washed with toluene then ethyl acetate and added to ammonium or sodium sulfate solution produced still lighter resin. These same observations were made with soluble soybean peroxidase and solvent-washed hulls. The use of solvent-washed hulls and polymerization with the enzyme in 0.4M ammonium sulfate produces low-color resins. The sulfate presumably reduces color by salting-in the colored impurities in the enzyme, preventing their release to the organic phase containing the polymer. Washing the hulls removes many of these color-causing impurities prior to the reaction.

The additional thermal stability of peroxidase from soybean hulls was demonstrated by heating soybeans at 90° C. for 30 minutes. Peroxidase activity measured following extraction from the resulting hulls was the same per gram hull in the 90° C. treated sample as the untreated control. Further, polymerization of bisphenol A in 45% n-propanol with soybean peroxidase produces a low-monomer color developer up to 45° C. reaction temperature at 50 units per gram monomer. The same reaction with Finnsugar or Sigma horseradish peroxidase succeeds only up to 20° C. Further, the reaction with soybean peroxidase succeeds at one-fourth the activity level required with horseradish peroxidase at 25° C.

Reaction temperature will vary with the substrate and the enzyme, most enzymes are temperature sensitive and a temperature should be selected which does not inhibit the reaction.

The reaction of the phenol proceeds at room temperature, but temperatures of about 0° to 70° C. can be used. The enzymes are temperature sensitive and can lose their activity if the reaction temperature becomes too high. However, some latitude exists, depending upon the solvent system which is used. Certain solvents can stabilize the enzyme and thereby permit the use of higher temperatures. There is evidence in the literature that temperatures up to 100° C. may be useful with some peroxidases.

The activity of peroxidases is pH dependent. The oxidative reactions are typically carried out at a pH in the range of about 1.5 to 12 and, preferably, 2 to 9 for most reactions, and, more preferably, about 2 to 6. A pH may be selected at which the enzyme is highly active. This will vary with the nature of the enzyme and the substrate. Buffers can be used to maintain pH, but are not usually required. One example of a useful buffer is a potassium phosphate buffer.

While reference is herein made to the bulk pH of the reaction system, those skilled in the art will appreciate that it is the pH in the micro-environment of the enzyme that is critical. Thus, where the phenol is dissolved in a water immiscible solvent and the enzyme solution is dispersed in the solution of the phenol, it is the pH of the enzyme solution which is critical.

It has also been found that, in general, the rate of reaction can be increased by optimizing the temperature of the reaction. Typically, the oxidative reactions are carried out at a temperature up to about 95° C. and preferably between about 35° and 75° C. and most preferably about 45 to 65° C. depending on the substrate.

Furthermore, it has been found that the rate of reaction can be increased by the presence of calcium ions such as calcium chloride. The calcium ion may be present at a concentration of up to about 100 mM or greater, preferably, at a concentration of about 10 to 100 mM.

Phenolic resins prepared in accordance with the present invention are useful in a variety of applications depending on the nature of the phenol and the molecular weight distribution of the resin. The resins are often mixtures of dimers, trimers, and higher molecular weight oligomers.

The molecular weight of the phenolic resin can be adjusted depending upon its particular end use. In one embodiment, the process of the present invention provides a phenolic resin which is useful as a developer in recording materials such as carbonless copy paper, heat-sensitive recording paper, electrothermographic recording paper and the like. The phenols used in developer resins are preferably para-substituted. Developer resins may range from about 500 to 5000 in molecular weight.

In another embodiment, the process of the present invention provides a phenolic resin which is useful as an adhesive. The phenols used in adhesives need not be parasubstituted. The resins typically range from about 1000 to 15,000 in molecular weight but molecular weights up to at least 30,000 are attainable. Among other factors affecting molecular weight are solvent selection, phenol selection, and reaction conditions.

Phenols which are preferred for reaction in the present invention are represented by the Formula (I):

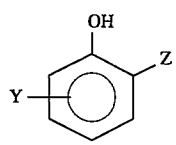

wherein Y and Z are selected from the group consisting of a hydrogen atom, a halogen atom, an alkyl group, an alkoxy group, an aryl group, an allyl group, a phenylalkyl group, a —COOR group, a —NR$^1$R$^2$ group, where R represents a hydrogen atom or a lower alkyl group, and R$^1$ and R$^2$ represent a hydrogen atom, an alkyl group, or a phenylalkyl group or Z in conjunction with the adjacent meta position forms a condensed benzene ring. Since polymerization proceeds via the ortho or para positions, when Y is at the ortho or para position, at least one of Y and Z must be a hydrogen atom or Z must form said condensed benzene ring. Y is preferably para to the phenolic hydroxyl group. Otherwise, the phenol adds as a terminal group as discussed below. At the para position, long chain alkyl groups have a tendency to slow the reaction. The reaction appears to proceed best when Y is p-phenyl, p-methoxy or p-halogen.

A single phenol or a mixture of phenols may be used in the process of the present invention. In certain applications it may be desirable to produce phenolic resins having certain terminal groups. This can be accomplished by reacting phenols in which the Y substituent is in the para position and Z is not a condensed ring with other phenols in which at least one of Y and Z is a hydrogen atom or Z is a condensed ring to provide copolymers. In this case the resin contains the Z substituent as a terminal group. When the para position is unsubstituted, polymerization proceeds via the ortho and/or para position and Z-substituted phenols can be incorporated mid-chain.

The alkyl group represented by Y and Z may contain up to 10 carbon atoms and include such alkyl groups as t-butyl, n-butyl, octyl, nonyl, etc. When R, R$_1$, and R$_2$ represent an alkyl group, it is typically a lower alkyl group having 1 to 4 carbon atoms.

Representative examples of alkoxy groups for Y and/or Z have 1 to 10 carbon atoms and include methoxy and ethoxy. When Y or Z is an aryl group, it is typically a phenyl group or substituted phenyl group such as a halogen-substituted phenyl group, an alkyl-substituted phenyl or a phenol group such as a 4'-phenol group.

Examples of a halogen atom include fluorine, chlorine, bromine and iodine.

Representative examples of phenylalkyl groups include benzyl, isopropylidene phenyl, butylidene phenyl, isopropylidene-4'-phenol, and butylidene-4'-phenol.

Specific examples of phenols which can be polymerized in accordance with the process of the present invention are phenol, 4-t-butylphenol, 4-n-butylphenol, 4-ethylphenol, cresol, p-phenylphenol, p-octylphenol, p-nonylphenol, p-hydroxybenzoic acid, 4-hydroxynaphthoic acid, p,p'-biphenol, 4-aminosalicylic acid, salicylic acid, methyl salicylate, ethyl salicylate, 4,4'-isopropylidenediphenol, ethyl 4-hydroxybenzoate, etc.

In one embodiment, a phenolic developer resin capable of reacting with an electron-donating color precursor and producing a visible image is represented by the formula (II):

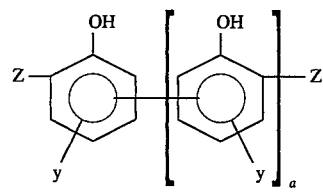

where n is greater than 2, the phenolic units of the resin are directly bonded to one another through positions ortho or para to the hydroxyl group, Y is not hydrogen and is present at a position meta or para (preferably para) to the hydroxyl group.

In accordance with another embodiment, the phenolic developer resin is represented by the formula (III):

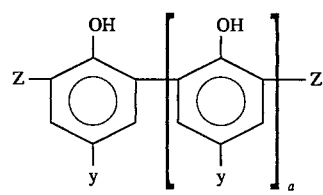

where n, Y, and Z are defined as in formula (II).

The phenolic resins can be homopolymers or copolymers, i.e., the individual Y or Z groups in a given phenolic developer resin may be the same or different and the Y groups may be located at different positions in accordance with the formula (II).

The phenolic developer resins may be metal-modified in a manner analogous to novolak developer resins to improve their reaction with color precursors and thereby improve the density and fastness of the image. For example, the phenolic developer resins can be modified by reaction with a salt of a metal selected from the group consisting of copper, zinc, cadmium, aluminum, indium, tin, chromium, cobalt, and nickel.

This modification can be made in an otherwise known manner. One method is by mixing and melting the resin with an alkanoate salt such as zinc propionate, zinc acetate, or zinc formate in the presence of an ammonium compound such as ammonium carbonate or ammonium acetate. The practice described in U.S. Pat. No. 4,173,684 can also be used.

The zinc-modified phenolic developer resins can also be formed by reacting zinc oxide or zinc carbonate and ammonium benzoate or ammonium formate with the resins in a manner analogous to the teachings in U.S. Pat. Nos. 4,165,102 and 4,165,103. Alternatively, the zinc-modified phenolic developer resins can be prepared by reaction with zinc chloride as shown in the examples below.

The metal content of the metal-modified phenolic developer resins should be more than 0.5 percent by weight and may range up to 25% by weight. Usually, a range of about 1.5 to 5 percent by weight is used.

In addition to chemically modifying the phenolic developer resins as described above, other means conventionally used in the art to improve the developing ability of phenolic developer resins, can be used in conjunction with the phenolic developer resins of the present invention. For example, acidic metal salts can be incorporated into coatings of the phenolic developer resins as described in U.S. Pat. Nos. 3,516,845 and 3,723,156. The phenolic developer resins of the present invention can also be used in combination with other phenolic developer resins or compounds and need not be used alone.

Recording materials utilizing phenolic developer resins to produce colored images from colorless or substantially colorless materials are well known. Specific examples of such recording materials include pressure-sensitive carbonless copying paper, heat-sensitive recording paper, electrothermographic recording paper, and the like. They are described in more detail in U.S. Pat. Nos. 2,712,507; 2,730,456; 2,730,457; 3,418,250; 3,432,327; 3,981,821; 3,993,831; 3,996,156; 3,996,405 and 4,000,087, etc. A photographic material has been developed which utilizes this method for forming colored images. See, for example, U.S. Pat. Nos. 4,399,209 and 4,440,846 to The Mead Corporation.

Recording materials can be prepared in a conventional manner. To provide a developer sheet, the phenolic developer resin may be dissolved in an appropriate solvent (typically acetone) and applied to the surface of the paper by blade or roll coating or the like. Alternatively, the developer resin may be used in the form of a resin grind analogous to the resin grinds described in U.S. Pat. No. 3,924,027 to Saito et al. For example, the resin may be pulverized and mixed with an organic high molecular compound such as starch or styrene-butadiene latex. This mixture is dispersed in water or a solvent that does not readily dissolve the phenolic developer resin or the high molecular compound and coated on an appropriate support.

The developer resin is usually applied in an amount of about 0.2 to 0.4 lbs. or resin/1300 sq. ft. (solids).

Where a self-contained recording material is desired, a mixture of the phenolic developer resin and microcapsules containing the developer can be coated upon a support as one layer, or the developer and the microcapsules can be applied in separate layers. For the preparation of photosensitive recording materials, see U.S. Pat. Nos. 4,399,209 and 4,440,846 which are incorporated herein by reference.

In addition to being useful as developer resins and as adhesives, phenolic resin products are useful in other applications. In particular, the lack of a methylene bridge imparts advantageous properties to the resins as counterparts. The resins should exhibit greater resistance to photolyric and thermal degradation, greater rigidity and greater conductivity making the resins potentially attractive for plasma resistance in photoresists, as conductive polymers, antioxidants for plastics, rubbers and the like, and as molding materials for high temperature applications. The higher density of functional hydroxy groups is being investigated for use in epoxy resin systems where higher crosslink densities should yield higher thermal deformation temperatures.

The resins produced in the present invention are also useful in composites analogous to epoxy resins. They are particularly useful in frictional composites such as brake linings, transmission bands, structural composites.

The process of the present invention is also useful in preparing lower molecular weight compounds such as dimers or trimers. Accordingly, in formula (II) and (III) above, the process should be useful in preparing compounds for which n is 1 or 2 as well as higher molecular weight compounds in which n is greater than 2.

In addition to being useful in preparing phenolic resins, soybean peroxidase and peroxidases from other legumes, rice and malvaceous plants are also believed to be useful in the following reactions: oxidative coupling of aromatic amines and indoles; oxidation of anions to free radicals (e.g., carboxylates, cyanide, thiolares, sulfite, ascorbate); oxidation of metallic mercury; hydroxylation of aromatic phenols and amines; oxidation of anions to inium ions (e.g., iodide, thiocyanate); oxidation of phenols to quinone methides and aromatic amines to imines; formation of disulfides from thiols, sulfoxides from sulfides and halides; formation of superoxide from thiols and oxygen; dehalogenation of halogenated phenols and aromatic amines; depolymerization of lignin and coal; iodination of aromatics; cleavage of uricares and sugars; oxidation of olefins to alcohols; cleavage of aldehydes to acids and ketones; demethylation of N-substituted aromatic amines; and treatment of wastewater for contaminants phenols and/or aromatic amines (see Alberti and Klibanov, supra).

In addition to being useful in the reactions discussed above, soybean peroxidase and hulls harvested and treated using the techniques described herein may also be useful in other applications previously thought to require the use of more expensive enzymes including the following: as biocides in pulp and paper mill streams (see U.S. Pat. No. 4,478,363); in enzymatic bleaching of Kraft pulp (see Intl publ No WO 87/00564, Intl Appln No PCT/US86/01476, Eriksson, KE, ChemAbstr 112:219038h, Ander, P., ChemAbstr 112:212969d); as a catalyst in immobilization of leachable toxic soil pollutants (see Shannon, M. J. R., et al. Appl. Env. Microbiol (1988) 54:1719–1723); in medical diagnostics in coupling to antibodies and detection with leuco-dyes (see U.S. Pat. Nos. 3,694,207; 4,828,983; 4,778,753; EP 218,083); in quinone dye synthesis (see Czch pat CS 247,596 B1); accelerated drying of lacquers (see Japn. Pat. 01163272); in synthesis of melanin-like dyes (see U.S. Pat. No. 4,609,544); in oxidative thickening of pectins (see U.S. Pat. No. 4,672,034); as bioamperometric sensors for phenol detection (see Bonakdar, M., ChemAbstr 112:90986j); in analytical determination peroxides (see Berlin, P., ChemAbstr 112:73352); as a bacteriacide to prevent tooth decay (see Grisham, M. B., ChemAbstr 112:117169j, Kessler, U.S. Pat. No. 4,476,108); in inactivation of mutagenic substances (see Chem Abstr 93:21203d, Japanese Pat. 55037180); in treatments and compositions to promote wound healing (see U.S. Pat. No. 4,503,037); in waste water treatment (see U.S. Pat. No. 4,623,465, Science 221:259–261 (1983), Enzyme Microb Technol 3:119-122 (1981), Davis, S., ChemAbstr 112:222683v, Alberti and Klibanor, supra), as a preventative for artherosclerosis (see Khanin, AL Chem Abstr 82:68359x); in activation of commercial enzymes (see Tressel, P., BBRC 92:781–786 (1980)); in quantitation and detection of gums (see Dickmann, R. S., Chem Abstr 111:55931k); in bleaching of fabrics (see Kirk, O., ChemAbstr 112:101222k); in stabilization or removal of phenols in beer (see Giovanelli, G., Chem Abstr 112:156624y); and in solubilization of coal (see Scott, C. D., ChemAbstr 113:26681z).

Of the foregoing applications, the soybean enzyme and hulls are particularly useful in wastewater treatment where they can be substituted for horseradish peroxidase.

The invention is illustrated in more detail by the following non-limiting examples.

EXAMPLE 1

Purification and use of horseradish peroxidase 100 g of a Tannic Acid solution was dissolved in 900 ml of 0.1M phosphate buffer of pH=6 to produce a 10% solution (W/V). The volume of the solution was adjusted with the phosphate buffer to 1000 ml. 200 ml of horseradish peroxidase solution from Finnsigar Biochemicals was stirred at room temperature and 20 ml of the 10% tannic acid solution was added over 5 minutes. The mixture was stirred for an additional 15 minutes and then poured into 800 ml of acetone with stirring. After 5 minutes the solution was filtered through a Whatman #4 paper filter. The precipitate was dissolved in 200 ml of water and centrifuged at 1500 Xg for 30 minutes. Following centrifugation, the supernatant was used as the source of enzyme in a biocatalytic process for preparing phenolic resin. At the end of the polymerization reaction, aqueous and organic phases separated spontaneously. The organic phase was filtered through diatomaceous earth to remove particles and then evaporated with steam to yield a light colored amber phenolic resin.

EXAMPLE 2 (Comparison).

The procedure of Example 1 was repeated except that the horseradish peroxidase was not treated with tannic acid prior to its use as a peroxidase enzyme in the polymerization reaction. At the end of the reaction a stable emulsion prevented separation of the aqueous and organic phases. The phenolic resin recovered from this reaction produced a red-brown resin. The phenolic resins produced in examples 1 and 2 were analyzed by HP gel-permeation and reverse phase chromatography which showed that the resins were very similar except for color.

EXAMPLE 3

Method of Harvesting Soybean Peroxidase: One kg of dry soybeans obtained from J. R. Kelly Company, Collinsville, Ill. was placed in a blender and homogenized in 5 l of water. The homogenate was filtered through four layers of cheesecloth and the filtrate saved. To 500 ml of the filtrate was added 75 ml of 10% tannic acid in 0.1M phosphate buffer. The mixture was centrifuged at 1500 Xg for 30 minutes and the supernatant saved. Protein in the supernatant was precipitated by pouring the supernatant into 3 volumes of acetone at room temperature. The acetone was decanted and the precipitate was dissolved in 500 ml of water. Protein contaminants were further removed by the addition of 2.5 ml of 50% $ZnCl_2$ in water. The Zn treated protein was centrifuged at 1500 Xg for 30 minutes and the supernatant was decanted. The supernatant was poured into 3 volumes of acetone to precipitate the Zn-treated protein. The acetone was decanted and the precipitate was dissolved in 100 ml of water and used as the source of soybean peroxidase enzyme.

Biocatalytic Polymerization of 4,4'-isopropylidenediphenol (Bisphenol A): The soybean peroxidase enzyme obtained above is employed as a biocatalyst in a normal polymerization of bisphenol A except that only 70% of the normal amount of enzyme is used (normal enzyme is from horseradish roots). 100 g of bisphenol A is dissolved in 60 ml of acetone and 140 ml of ethyl acetate. 3500 units of the soybean peroxidase at 14 units/mg protein (0.25g) are dissolved in 400 ml of deionized water. Both solutions are added to a one liter, three-necked round bottom flask and stirred at 300 rpm's. 67 ml of a 15% hydrogen peroxide solution is added over an approximately 6 hour period. Upon completion of the reaction, phase separation occurs spontaneously and the product is easily recovered from the organic phase by evaporation. The product shows the same distribution of polymer and same glass-transition temp Tg=83° C. as obtained when using horseradish peroxidase and bisphenol A except that no residual monomer is detected. Thus, using ⅔ the normal amount of enzyme, a 100% yield of bisphenol A polymer is obtained using the pre-treated soybean peroxidase.

EXAMPLE 4

A volume of a detergent (sodium dodecyl sulfate) is added to a solution of horseradish peroxidase to give a 2% final concentration of detergent (W/V). The protein is precipitated by pouring the mixture into 3 volumes of isopropanol. The precipitate is dissolved in a minimal volume of water and assayed for peroxidase. The treated peroxidase is mixed with bisphenol A dissolved in 20% acetone in the ratio of 50 units peroxidase per gram of bisphenol A per 6 ml of 20% acetone. A 15% hydrogen peroxide solution was added in the ratio of 0.18 ml per g of bisphenol A over a period of one hour. After one hour the mixture was centrifuged at 1500 ×g for 15 minutes and the bisphenol A resin recovered. The supernatent was used as the source of enzyme in a normal polymerization reaction.

EXAMPLE 5

Soybeans are cracked in a grinding mill, extracted with acetone, and soaked in water to loosen the hulls. The hulls float to the surface and are isolated by pouring them onto a screen. The hulls are homogenized in 0.4M ammonium sulfate filtered through cheese cloth and the homogenate is separated into three samples which were treated as follows:

Sample 1: The homogenate is adjusted to 30% isopropanol (V/V), and slurried with activated carbon at 1% W/V concentration. The slurry is stirred for a few minutes after which the mixture is filtered through celite on a Whatman GF/F glass fiber filter (0.7 micron pore size). The filtrate is used as a source of purified soybean peroxidase.

Sample 2: The homogenate is slurried in water with 0.3% activated carbon. The slurry is stirred, filtered through celite and used as a source of purified soybean peroxidase.

Sample 3: The homogenate was adjusted to 20% acetone (W/V) and slurried with 1% activated carbon (W/V). The mixture was filtered through celite. The activated carbon was washed with 30% isopropanol in water (W/V) and the isopropanol wash was used as a source of purified soybean peroxidase.

In each of the three procedures, significant amounts of impurities are removed from the soybean peroxidase in an economical manner to allow the use of the purified enzyme in a wide variety of applications where these impurities might otherwise interfere.

EXAMPLE 6

Soybean seed hull extract was mixed with an equal volume of 20% t-butyl phenol in isopropanol. 0.5 volumes of water was added and the mixture centrifuged at 1500 ×g for 15 minutes. The aqueous layer was removed by siphoning and adjusted to 6–10% KCl solution W/V with solid potassium chloride. The treated extract was poured into 4 volumes of acetone. The acetone solution was centrifuged and decanted. The precipitate was dissolved in water to yield purified soybean peroxidase at 4M KCl concentration. The treated soybean peroxidase was used in the polymerization of bisphenol A to produce a low molecular weight polymer of bisphenol A.

EXAMPLE 7

The procedure of Example 6 was repeated using t-butyl phenol as the purifying agent in n-propanol to provide purified soybean peroxidase.

EXAMPLE 8

The procedure of Example 6 was repeated using bisphenol A as the purifying agent in isopropanol to provide purified soybean peroxidase.

EXAMPLE 9

The procedure of Example 6 was repeated using bisphenol A as the purifying agent in n-propanol to provide purified soybean peroxidase.

In each of Examples 7–9, the soybean peroxidase enzyme is used in the polymerization of bisphenol A to provide a bisphenol A resin similar to that obtained in Example 6 and 10. Examples 6–9 are useful with hulls isolated from aged beans (over 1 yr. old) or hulls contaminated with significant amounts of bean material as well as fresh hulls.

EXAMPLE 10

Horseradish root extract was mixed with an equal volume of 20% t-butyl phenol in isopropanol. 0.5 Volumes of water was added and the mixture centrifuged at 1500 ×g for 15 minutes. The aqueous layer was removed by siphoning and mixed with about 6–10% KCl solution. The treated extract was poured into 4 volumes of acetone. The acetone solution was centrifuged and decanted. The precipitate was dissolved in water to yield purified horseradish peroxidase. The treated horseradish peroxidase was used in the polymerization of bisphenol A to produce a low molecular weight polymer of bisphenol A.

EXAMPLE 11

The procedure of Example 10 was repeated using t-butyl phenol as the purifying agent in n-propanol to provide purified horseradish peroxidase.

EXAMPLE 12

The procedure of Example 10 was repeated using bisphenol A as the purifying agent in isopropanol to provide purified horseradish peroxidase.

EXAMPLE 13

The procedure of Example 10 was repeated using bisphenol A as the purifying agent in n-propanol to provide purified horseradish peroxidase.

In each of Examples 11–13, the horseradish peroxidase enzyme is used in the polymerization of bisphenol A to provide a bisphenol A resin similar to that obtained in Examples 5 and 9.

EXAMPLE 14

The economic and practical utility of soybean seed hulls was tested as a substitute catalyst in the synthesis of bisphenol A polymer, a well-established color developer which can be made in a predicable manner using free horseradish or soybean peroxidase in solution. Ground soybean hulls were obtained from Cargill, Inc. of Sidney, Ohio. The hulls were screened through a 30 mesh screen and the −30 mesh hulls were used in the following examples. The reaction conditions were 100 g hulls added to 840 ml aqueous solution and mixed with 200 g bisphenol A dissolved in 360 ml n-propanol. Fifteen percent hydrogen peroxide was added gradually over 2.5 hours until 60 mole percent was added. No peroxide excess was indicated by using starch-iodide test strips during the reactions. Stirring was at 300 rpm and the exothermic polymerization was allowed to proceed without temperature control. Typically, the temperature may reach a maximum of 40° C. At the end of the reaction, the mixture was centrifuged at 1,500×g for 10 minutes and the aqueous supernatant decanted. Occasionally, a 2-fold dilution with water is required for good separation on centrifugation. The polymeric resin and hulls were stirred with 1 liter ethyl acetate, recentrifuged and the supernatant filtered through a Whatman GF/F Glass fiber filter. The ethyl acetate was separated from the polymer by evaporation on a steam bath followed by a hot plate. The yield of resin was 60–90% of the starting monomer.

Of the above mentioned reactions, soybean peroxidase and hulls harvested and treated using the technique described herein are particularly useful in the following reactions: oxidation of a-unsaturated alcohols; dealkylation of aromatic methoxides such as methoxybenzenes; N-dealkylation of N-substituted amines such as N-dealkylation of N,N-dialkylsubstituted aromatic amines; oxidation of aromatic sulfides; halogenation of organic compounds; hydroxylation of phenolic compounds; and the oxidative polymerization of aromatic compounds such as anilines and 2-6-disubstituted phenols.

The present invention as defined above is more fully described in the following examples which are intended to specifically illustrate representative embodiments of the invention.

α-Unsaturated alcohols such as benzylic alcohols, propargylic alcohols and allylic alcohols, examples of which include benzyl alcohol, veratryl alcohol, allyl alcohol, propargyl alcohol, crotyl alcohol 2-phenylethanol, 2-pyridyl carbonol and furfuryl alcohol are oxidized by soybean peroxidase in the presence of a peroxide to produce aromatic aldehydes as illustrated in Example 15 where veratryl alcohol (3,4-dimethoxybenzyl alcohol) is oxidized to veratryl aldehyde.

EXAMPLE 15

Oxidation of Veratryl Alcohol

Preparation of Soybean Peroxidase Solution: Purified soybean peroxidase was lyophilized to give a powder at 120 purpurogallin units (as defined by Sigma) per mg. Purification was done with addition of 5 mM CaCl2, but without buffers or other non-volatile substances which would carry over with the enzyme in the powder. Lyophilization typically yielded 4.5 g from 60 ml. Assay by the Bradford method using BSA as a standard indicated that the solid was 60% protein by weight. Capillary electrophoresis monitored at 200 nm showed about 95% of absorbance coincident with soybean peroxidase peak. Using the extinction coefficient reported for heme in HRP (103 uM-1 at 403 nm in 0.1M Tris pH 7), and the reported molecular weight of SBP (37,000), the solid was 60% peroxidase by weight.

Preparation of peroxide stock solution: 1.5 ml of 30% hydrogen peroxide was diluted to 100 ml with water to provide a 0.147M stock solution of hydrogen peroxide.

0.1 ml soybean peroxidase (120 purpurogallin units/ml) stock solution was added to 3 ml veratryl alcohol solution (1 g veratryl alcohol in 750 ml water) and vortexed in a test tube. 20 µl peroxide stock solution was added, mixed and the solution poured into a 1 cm path, 4 ml quartz cuvette. Using a Shimadzu UV-160 double beam recording spectophotometer, the change in absorbance of the sample compared to a reference cuvette containing 3 ml veratryl alcohol solution only was monitored every minute by scanning wavelengths from 500 to 200 nm. The peak wavelength of 308 nm was identified as veratryl aldehyde and was used for further monitoring. The kinetics of the reaction were determined from the linear portion of the increase in absorbance.

To determine the effects of pH on the oxidation of veratryl alcohol, a veratryl alcohol stock solution containing 20 mM CaCl$_2$ was divided into 9 samples and each sample treated with HCl to provide 9 samples ranging in pH from 1.25 to 3. 3 ml of solution was withdrawn from each sample and the change in absorbance (dA) of veratryl alcohol in each sample was measured at 308 nm at room temperature. Results are shown in Table 1.

TABLE I

| pH | dA per minute at 308 nm |
|---|---|
| 1.25 | 0.0045 |
| 1.35 | 0.0361 |
| 1.65 | 0.2358 |
| 1.85 | 1.611 |
| 2.15 | 0.945 |
| 2.35 | 0.2243 |
| 2.55 | 0.1093 |
| 2.85 | 0.0587 |
| 3 | 0.0119 |

As seen from Table 1, a narrow pH optimum occurs at a pH of around 2. Substitution of buffers in the assay mix at 0.1M ranging from pH 1 to 12.5, every 0.5 pH units, showed the same optimum with an activity of 0.2265 in 0.1M KCl/HCl at pH 2, suggesting that ionic strength inhibits activity.

To determine the effects of temperature on veratryl alcohol oxidation at a pH of 2, 5 samples of a veratryl alcohol stock solution without CaCl$_2$ were obtained and the absorbance of veratryl alcohol was measured at varying temperatures. The samples were incubated in a circulating water bath and cuvette blocks were preheated by connection with the same bath. The test cuvette was left empty in the block to equilibrate prior to assay. Enzyme and peroxide stock solutions were stored at room temperature. Assay was initiated by pouring the alcohol solution into the cuvette, adding 0.1 ml enzyme, inverting, adding 20 ul peroxide, inverting, and immediately starting to record change in absorbance. Results are shown in Table 2.

TABLE 2

| Temperature, °C. | dA per minute at 308 nm |
|---|---|
| 25 | 1.427 |
| 35 | 2.358 |
| 45 | 3.17 |
| 55 | 0.3467 |
| 65 | 0.0018 |

As seen from Table 2, there is a linear two-fold increase in activity up to at least 45 degrees, followed by inactivation of enzyme and lower activity. These results reflect the effect of temperature at pH 2 and the interaction of the alcohol with SBP. A mildly elevated temperature clearly enhances catalytic rate with veratryl alcohol.

Alkyl aromatic ethers such as dialkoxybenzenes, trialkoxybenzenes and tetraalkoxybenzenes, e.g., 1,2,4,5 tetramethoxybenzene are dealkylated by soybean peroxidase in the presence of a peroxide to produce aromatic ketones or quinones as illustrated in Example 16 where 1,4-dimethoxybenzene, 1,2,3-trimethoxybenzene and 1,3,5-trimethoxybenzene are oxidatively demethylated to the corresponding ketone and/or quinone products.

EXAMPLE 16

Demethylation of Methoxybenzenes

Using assay methods described in Example 15, three methoxybenzenes were tested for oxidation by soybean peroxidase (SBP). These compounds were: 1,4-Dimethoxybenzene (DMB), 1,2,3-Trimethoxybenzene (TMB) and 1,3, 5-Trimethoxybenzene (TMB). Stock solutions were prepared by heating 1 g (0.5g 1,3,5-TMB) in 750 ml water to 60 deg C on a stirring hot plate, allowing the solution to cool to room temperature and adjusting the pH to 2 with HCl. Assays were performed as described in Example 1. Initially, a scan of wavelengths from 500 to 200 nm every minute was done during each substrate oxidation to find suitable wavelengths to monitor for the corresponding quinone products. Results are shown in Table 3.

TABLE 3

| | dA per minute - Substrate (λnm) | | | |
|---|---|---|---|---|
| Temp., °C. | 1,4-DMB (250) | 1,4-DMB (310) | 1,2,3-TMB (289) | 1,3,5-TMB (286) |
| 25 | 1.0134 | 0.3566 | 0.0147 | ND |
| 35 | 1.1306 | 0.3942 | 0.0272 | 0.0282 |
| 45 | 1.817 | 0.745 | 0.0893 | 0.474 |
| 55 | 2.73 | 1.088 | 1.1161 | 0.097 |
| 65 | 2.99 | 0.437 | 0.0301 | 0.1724 |
| 75 | 0.883 | 0.129 | 0.0142 | 0.0262 |
| 85 | 0.0619 | 0.0237 | ND | ND |
| 95 | 0.0777 | 0.0296 | ND | ND |

ND = not determined

As seen from Table 3, increasing temperature enhances the rate of demethylation of methoxybenzene with an optimal temperature around 65° C. at a pH of 2.

Dealkylation of N,N-dialkyl aromatic amines is accomplished by soybean peroxidase in the presence of a peroxide to form N-alkyl aromatic amines as illustrated in Example 17 where N,N-dimethylanthranilic acid methyl ester is oxidatively demethylated to form N-methylanthranilic acid methyl ester.

EXAMPLE 17

Demethylation of N,N-Dimethylanthranilic acid Methyl Ester

N,N-Dimethylanthranilic acid methyl ester (DMA) and the product of N-demethylation, N-methylanthranilic acid methyl ester (NMA), were purchased from TCI America (Portland, Oreg.). Absorption spectrum of the product NMA showed peaks at 295 and 379 nm in 25 mM acetate, pH 4.5 buffer. Oxidation of DMA using soybean peroxidase (120 ppu) in pH 4.5 buffer showed increase in absorbance peeks at both these wavelengths, indicating N-demethylation. Using 1 g. (5mM) DMA in 25 mM acetate, pH 4.5, 120 ppu SBP and 1 mM H202, the increases observed were: 295 nm - 0.727 AU per min; 379 nm –0.403 AU per min. To optimize N-demethylation, the effect of pH was studied using 25 mM buffers at the appropriate pH. The results are shown in Table 4.

TABLE 4

| pH | dA per min at 379 nm |
| --- | --- |
| 1 | 0.005 |
| 2 | 0.2603 |
| 3 | 0.099 |
| 4 | 0.181 |
| 5 | 0.2401 |
| 6 | 0.1095 |
| 7 | 0.0065 |

Results showed optimal pH for N-demethylation at pH 2 and pH 5 corresponding to an increase in absorbance at 279 nm expected for formation of the product, NMA.

Aromatic sulfides are oxidized by soybean peroxidase in the presence of a peroxide to produce sulfoxides and sulfones as illustrated in Example 4 where methyl p-tolyl sulfide is oxidized to methyl p-tolyl sulfoxide and sulfone. The reaction has been observed to be stereospecific and yields a concentration of one enantiomer when the sulfur atom is a chiral center.

EXAMPLE 18

Oxidation of Aromatic Sulfides

Methyl p-tolyl sulfide (MTS), and the enantiomeric oxidation products (R)-(+)-methyl tolyl sulfoxide (MTSO) and (S)-(–)-methyl tolyl sulfoxide, were purchased from Aldrich (Milwaukee, Wis). A stock solution of MTS was prepared by adding 1 g MTS to 750 ml water and heating at 60° C. for 15 min. A warm stock solution was used for all assays to maintain the substrate in solution. The products, (±) MTSO showed maximal absorbance at 279 nm in 25 mM glycine pH 3.5, with a minor peak, assumed to be methyl tolyl sulfone at 308 nm. At pH 2 these peaks shift to 274 and 311 nm, respectively. The results are shown in Table 5.

Assays with MTS were done with 120 ppu SBP and 1 mM $H_2O_2$. On addition of peroxide, absorbance at 279 nm (pH 3.5) increased according to the following data as shown in Table 5.

TABLE 5

| Time of Reaction, Min. | Absorbance Units at 279 mm |
| --- | --- |
| 0 | 0.089 |
| 1 | 0.383 |
| 2 | 0.394 |
| 7 | 0.526 |

The effect of pH on the oxidation of MTS was studied to optimize the reaction. Buffers were used at the indicated pH at 25 mM concentration. The results are shown in Table 6.

TABLE 6

| pH | dA per min at 279 nm |
| --- | --- |
| 1 | 0.0348 |
| 2 | –0.1376 |
| 3 | 0.1042 |
| 3.5 | 0.218 |
| 4 | 0.0893 |
| 4.5 | 0.0017 |

As seen from Table 5, the enzymatic oxidation of MTS to MTSO shows a pH optimum of 3.5 based on the above data. At pH 2, the decline in absorbance at 279 nm corresponds to an increase in absorbance at 308 nm, indicating further oxidation to the sulfone ($MTSO_2$).

Therefore, oxidation can be predetermined by controlling the pH. Oxidation of sulfides to sulfoxides is especially useful where enzymatic catalysis yields an enrichment in an enantiomer. Such products may be selective for biological targets with such uses as pesticides of pharmaceuticals.

Oxidation was measured at 308 nm and pH 2 to demonstrate further conversion to the sulfones. The results are shown in Table 7.

TABLE 7

| Time of Reaction, Min | Absorbance Units at 308 nm |
| --- | --- |
| 0 | 0.21 |
| 1 | 0.293 |
| 2 | 0.35 |
| 3 | 0.381 |
| 4 | 0.401 |

The effect of temperature on aromatic sulfide oxidation was investigated at pH 3.5 using MTS. Conditions were 120 ppu SBP, 25 mM Glycine, 2 mM MTS, 1 mM $H_2O_2$. The results are shown in Table 8.

TABLE 8

| Temperature, °C. | dA per min at 279 nm |
| --- | --- |
| 25 | 0.0607 |
| 35 | 0.0824 |
| 45 | 0.1012 |
| 55 | 0.1735 |
| 65 | 0.2563 |
| 75 | 0.1065 |
| 85 | 0.0908 |

The results show that temperature can be used to enhance the oxidation of sulfides to sulfoxides, with an optimal temperature of 65 degrees C at pH 3.5. The effect of temperature on the enantiomeric composition of the sulfoxide product has not been determined.

Oxidative halogenation such as chlorination, bromination and iodination is catalyzed by soybean peroxidase as illustrated in Example 19 where dimedone is oxidatively chlorinated to 2-chlorodimedone.

EXAMPLE 19

Chlorination of Dimedone

A stock solution (9.5 mM dimedone) was prepared by adding 1 g. 5,5-dimethyl-1,3-cyclohexane dione (dimedone) to ml water. The solution was stirred to dissolve the dimedone and the pH adjusted to 2 with HCl. Chlorination of dimedone was catalyzed by soybean peroxidase (120 ppu) at pH 2 and 1 mM $H_2O_2$. Increase in absorbance at 307 nm, corresponding to the absorbance maximum of 2-chlorodimedone was followed at room temperature and is shown in Table 9.

TABLE 9

| Time of Reaction, min | Absorbance Units at 307 nm |
|---|---|
| 0 | 0.175 |
| 1 | 0.275 |
| 2 | 0.510 |
| 3 | 0.800 |
| 7 | 0.868 |

The effect of temperature on cholrination of dimedone was studied under these conditions. Reactions were performed as described above with increasing assay temperature. The results are shown in Table 10.

TABLE 10

| Temperature, °C. | dA per min at 307 nm |
|---|---|
| 25 | 0.1066 |
| 35 | 0.1204 |
| 45 | 0.1962 |
| 55 | 0.1792 |
| 65 | 0.0155 |
| 75 | 0.0181 |

Table 10 shows that increasing temperature can be used to enhance the oxidative chlorination of dimedone with an optimal temperature of about 45° C. These results raise the question of the role of chloride oxidation in other oxidative reactions. For example, a comparison of the rates of oxidation of 1,4-dimethoxybenzene at pH 2 where the pH was adjusted with HCl in one case and with $HNO_3$ in a second case is shown in Table 11.

TABLE 11

| Acid | dA 310 nm per min | dA 250 nm per min |
|---|---|---|
| HCl | 0.3273 | 1.275 |
| $HNO_3$ | 0.2934 | 0.7202 |

The results shown in Table 11 indicate that chloride oxidation may enhance O-demethylation of DMB at pH 2. However, since oxidation also occurs without chloride present, chloride is not required and direct oxidation of DMB appears to be catalyzed by soybean peroxidase.

Soybean peroxidase catalyzes the hydroxylation of phenolic compounds through molecular oxygen and a reducing agent rather than through the traditional oxidant, hydrogen peroxide. Oxygen mediated hydroxylation of phenols by soybean peroxidase as illustrated in Example 20 where tyrosine is oxidatively hydroxylated to dihydroxyphenylalanine (DOPA). The preferred reducing agent is dihydroxyfumarate.

EXAMPLE 20

Hydroxylation of Tyrosine

Tyrosine, 0.2 g was added to 150 ml water and HCl was added until the tyrosine dissolved at about pH 3. Dihydroxyfumaric acid (DHF), 0.44 g was added to 100 ml water and dilute (1%) sodium hydroxide was added until the acid dissolved at about pH 3.

Hydroxylation of tyrosine was achieved by mixing 2 ml tyrosine solution, 1 ml 0.1M buffer selected from a range of pH 1–13, 0.1 ml soybean peroxidase at 10 mg/ml and last, adding 0.1 ml DHF stock solution. The reference curvette contained the same mixture of tyrosine, buffer and DHF stock solutions. No hydrogen peroxide was used in these reaction. Dissolved oxygen from air served as the source of oxidant. Peak wavelength corresponding to DHF, determined by DHF absorbance in the solution, was monitored for loss in absorbance, indicating consumption of the reducing agent and hydroxylation of the phenol. Oxidation was followed by monitoring wavelengths from 500 to 200 nm at zero time and 1 minute of reaction. The absorbance difference at the wavelength corresponding to loss of DHF was recorded. The effect of pH on oxidation of DHF and hydroxylation of tyrosine is shown in Table 12.

TABLE 12

| pH | dA per min | λ, nm |
|---|---|---|
| 1 | 0 | 310 |
| 2 | 0.012 | 315 |
| 3 | 0.726 | 321 |
| 3.5 | 0.886 | 318 |
| 4 | 0.065 | 319 |
| 4.5 | 0.391 | 320 |
| 5 | 1.897 | 303 |
| 5.5 | 0.971 | 302 |
| 6 | 2.226 | 302 |
| 6.5 | 2.134 | 302 |
| 7 | 0 | Interference |
| 7.5 | 0 | from Tris |
| 8 | 0 | buffer |
| 8.5 | 1.098 | 305 |
| 9 | 1.705 | 304 |
| 9.5 | 1.66 | 302 |
| 10 | 0.768 | 302 |
| 10.5 | 1.372 | 302 |
| 11 | 1.988 | 302 |
| 11.5 | 0.075 | 305 |
| 12 | 0.069 | 305 |
| 13 | 0 | 305 |

Table 12 shows that optimal hydroxylation is around pH 3.5, 6 and 11. Non-enzymatic consumption of DHF, measured with boiled SBP was minimal.

Oxidative polymerization of anilines to form polyanilines is catalyzed by soybean peroxidase in the presence of a peroxide as shown in Example 21 where 4-ethyl aniline was polymerized. It is known that aniline can be polymerized to form an intrinsically conductive polymer (ICP). Intrinsically conductive polymers are a class of polymers or non-metallic materials with electrical properties typically found only in metals and semiconductors. The ICP materials are unique and highly valued products for use in many industrial and consumer applications.

EXAMPLE 21

Polymerization of 4-ethyl aniline 4-ethyl aniline was polymerized using soybean peroxidase and hydrogen peroxide as follows: One gram 4-ethyl aniline was mixed with 750 ml water. 1.5 ml 30% $H_2O_2$ was diluted to 100 ml with water (0.147 M). Soybean peroxidase was prepared at 10 mg/ml (120 ppu/mg). 0.1 ml SBP was added to 750 ml 4-ethyl aniline solution. The reaction mixture was stirred on a stir plate at room temperature and 4 ml dilute peroxide was added slowly over 10 minutes. The reaction turned orange and cloudy. The product was salted out with MgCl2 and treated with 50% NaOH to precipitate MgOH and the polymer. The polymer was collected by centrifugation and dried. The molecular weight of the resulting polymer was determined by gel permeation chromatography in the usual manner using polystyrene standards.

The resulting product had a number average molecular weight of 295 and a polydispersity of 1.3 compared with polystyrene standards indicating that soybean peroxidase catalyzed the oxidative polymerization of aniline to form a polyaniline.

Polyphenyleneoxides can be prepared by the soybean catalyzed, oxidative polymerization of phenols which are substituted (blocked) at the 2,6 positions as shown in Example 22 where 2,6-dimethyl phenol is polymerized to form poly(dimethyl)phenyleneoxide.

EXAMPLE 22

Polymerization of 2.,6-dimethyl phenol 30.5 grams of 2,6-dimethyl phenol is dissolved in 300 ml of isopropyl alcohol in a jacketed one liter round bottom flask heated to 50° C. 188 ml distilled water and 12 ml of a soybean peroxidase solution containing 1500 purpurogallin units is added to the 2,6-dimethyl phenol solution and stirred. 85 ml of a 10% hydrogen peroxide solution is added to the above solution while stirring over a period of 11.5 hours. Upon completion of the hydrogen peroxide addition, the stirring is stopped and polyphenylene oxide precipitates from the solution.

Having described the invention in detail and by reference to preferred embodiments thereof, it will be apparent that modifications and variations are possible without departing from the scope of the invention defined in the appended claims.

What is claimed is:

1. A method for carrying out a biocatalytic oxidative reaction selected from the group consisting of oxidation of sulfides, O-dealkylation of alkyl aryl ethers, N-dealkylation of aromatic amines, halogenation of halogen-reactive compounds, and polymerization of aromatic amines, which method comprises preparing a solution of a reactive substrate selected from the group consisting of sulfides, alkyl aryl ethers, aromatic amines, and halogen-reactive compounds in an organic or aqueous medium and contacting said solution with soybean peroxidase in the presence of a peroxide.

2. The method of claim 1 wherein said peroxide is hydrogen peroxide.

3. The method of claim 2 wherein said biocatalytic oxidative reaction is carried out in the presence of about 10 to 100 mM calcium ions.

4. The method of claim 1 wherein said biocatalytic oxidative reaction is the oxidation of sulfides and the sulfides are aryl sulfides.

5. The method of claim 4 wherein said alkyl aryl sulfide is methyl p-tolyl sulfide.

6. The method of claim 1 wherein said biocatalytic oxidative reaction is the O-dealkylation of alkyl aryl ethers and said alkyl aryl ethers are methoxybenzenes.

7. The method of claim 6 wherein said methoxybenzene is selected from the group consisting of 1,4-dimethoxybenzene, 1,2,3-trimethoxybenzene, 1,3,5-trimethoxybenzene, 1,2,4,5-tetramethoxybenzene, and mixtures thereof.

8. The method of claim 1 wherein said biocatalytic oxidative reaction is the N-dealkylation of aromatic amines and said aromatic amines are N,N-dimethyl aromatic amines.

9. The method of claim 8 wherein said N,N-dimethyl aromatic amine is N,N-dimethyl-anthranilic acid methyl ester.

10. The method of claim 1 wherein said biocatalytic oxidative reaction is the polymerization of aromatic amines.

11. The method of claim 10 wherein said aromatic amine is 4-ethyl aniline.

12. The method of claim 10 wherein said aromatic amine is aniline.

13. The method of claim 10 wherein said polymerization results in an intrinsically conductive polymer (ICP).

14. The method of claim 10 wherein said aromatic amine is aniline and said polymerization results in an intrinsically conductive polymer (ICP).

15. The method of claim 1 wherein said biocatalytic oxidative reaction is the oxidative halogenation of a halogen-reactive compound.

16. The method of claim 15 wherein said halogen-reactive compound is 5,5-dimethyl 1,3-cyclohexane dione.

* * * * *

UNITED STATES PATENT AND TRADEMARK OFFICE
CERTIFICATE OF CORRECTION

PATENT NO. : 5,508,180
DATED : April 16, 1996
INVENTOR(S) : Mark A. Johnson et al.

It is certified that error appears in the above-indentified patent and that said Letters Patent is hereby corrected as shown below:

Col. 22, Claim 4, line 13, before "aryl" insert --alkyl--.

Signed and Sealed this

Second Day of July, 1996

Attest:

BRUCE LEHMAN

Attesting Officer    Commissioner of Patents and Trademarks